(12) United States Patent
Koenen et al.

(10) Patent No.: US 11,389,299 B2
(45) Date of Patent: Jul. 19, 2022

(54) ORTHOPAEDIC IMPLANT AND FIXATION SYSTEM

(71) Applicant: ATRO Medical B.V., Nijmegen (NL)

(72) Inventors: Jacob Koenen, Sittard (NL); Edwin Norbertus Antonius Maria Daamen, Born (NL); Jan Hunik, Nijmegen (NL); Tony van Tienen, Nijmegen (NL)

(73) Assignee: ATRO Medical B.V., Nijmegen (NL)

( * ) Notice: Subject to any disclaimer, the term of this patent is extended or adjusted under 35 U.S.C. 154(b) by 127 days.

(21) Appl. No.: 16/954,214

(22) PCT Filed: Dec. 21, 2018

(86) PCT No.: PCT/NL2018/050872
§ 371 (c)(1),
(2) Date: Jun. 16, 2020

(87) PCT Pub. No.: WO2019/125167
PCT Pub. Date: Jun. 27, 2019

(65) Prior Publication Data
US 2020/0360149 A1    Nov. 19, 2020

(30) Foreign Application Priority Data
Dec. 21, 2017    (NL) .................................. 2020144

(51) Int. Cl.
*A61F 2/38* (2006.01)
*A61F 2/30* (2006.01)

(52) U.S. Cl.
CPC ........ *A61F 2/3872* (2013.01); *A61F 2/30771* (2013.01); *A61F 2002/305* (2013.01); *A61F 2002/3085* (2013.01); *A61F 2002/30331* (2013.01); *A61F 2002/30578* (2013.01); *A61F 2002/30795* (2013.01)

(58) Field of Classification Search
CPC combination set(s) only.
See application file for complete search history.

(56) References Cited

U.S. PATENT DOCUMENTS 8,377,138 B2 * 2/2013 Reo .......................... A61F 2/442
                                                623/17.13
2008/0243260 A1 * 10/2008 Lee ...................... A61F 2/3868
                                                623/20.29

(Continued)

*Primary Examiner* — Javier G Blanco
(74) *Attorney, Agent, or Firm* — N.V. Nederlandsch Octrooibureau; Catherine A. Shultz

(57) ABSTRACT

A prosthesis assembly (100) for orthopaedic implantation comprises a prosthesis body (110) and an attachment portion (112) coupled to the prosthesis body (110) for attaching the prosthesis assembly (100) to a bone by way of a bone anchor (120) or other fixating means. The attachment portion (112) comprises an opening (130) having a receiving portion (132) with a first cross-sectional transverse width and a retaining portion (134) extending from the receiving portion (132), the retaining portion (134) having a second cross-sectional transverse width, which is less than the first cross-sectional transverse width. A system comprising the prosthesis assembly (100) includes a bone anchor (120) having a fastening member (124) for engaging the opening (130) and a stem (122) for securing to the bone.

14 Claims, 5 Drawing Sheets

(56) References Cited

U.S. PATENT DOCUMENTS

| | | | |
|---|---|---|---|
| 2013/0190873 A1* | 7/2013 | Mansmann | A61F 2/3872 623/14.12 |
| 2013/0268074 A1* | 10/2013 | Vowles | A61F 2/3872 623/14.12 |
| 2013/0312897 A1 | 11/2013 | Vowles | |
| 2016/0235538 A1 | 8/2016 | Van Tienen | |
| 2017/0014237 A1 | 1/2017 | Koenen et al. | |

* cited by examiner

ORTHOPAEDIC IMPLANT AND FIXATION SYSTEM

FIELD OF THE INVENTION

The present invention relates to an orthopaedic implant (e.g. an implant for interposition between bone-bone, cartilage-cartilage, soft tissue surfaces or any combination thereof) and an associated fixation system. More particularly, the prosthesis system comprises a replaceable prosthesis body, such as a replaceable joint prosthesis assembly.

BACKGROUND ART

Orthopaedic implants and fixation systems for the same are known. One example of a knee meniscus prosthesis is disclosed in WO2015/057056, which describes a joint prosthesis body made of a first biocompatible non-resorbable material and an anchoring element made of a second biocompatible non-resorbable material. The anchoring element comprises a plug and a cable with a disc at its distal end. To secure the prosthesis in place, the cable is passed through the bore in the prosthesis and the plug secured within a bone tunnel.

SUMMARY OF THE INVENTION

The present invention seeks to provide an improved prosthesis assembly for orthopaedic implantation in which the prosthesis can be replaced without disturbing the associated bone anchor from its seating.

According to a first aspect of the present invention, there is provided a prosthesis assembly for orthopaedic implantation, comprising a prosthesis body and an attachment portion coupled to the prosthesis body, wherein the attachment portion comprises an opening having a receiving portion with a first cross-sectional transverse width and a retaining portion extending from the receiving portion, the retaining portion having a second cross-sectional transverse width, which is less than the first cross-sectional transverse width. Preferably, the prosthesis body comprises a knee meniscus replacement. The prosthesis body may also take other forms. For example, the prosthesis body can comprise a prosthetic meniscus or labrum for use in other parts of the body comprising an articular surface, e.g. a hip joint, shoulder, mandibular joint, etc.

According to a second aspect of the invention, there is provided a prosthesis system comprising a bone anchor and a prosthesis assembly. The prosthesis assembly comprises a prosthesis body and an attachment portion coupled to the prosthesis body, wherein the attachment portion comprises an opening having a receiving portion with a first cross-sectional transverse width and a retaining portion extending from the receiving portion, the retaining portion having a second cross-sectional transverse width, which is less than the first cross-sectional transverse width. The bone anchor comprises a fastening member configured to engage the opening in the attachment portion of the prosthesis and a stem configured to be secured to a body structure, e.g. a bone. Optionally, the system can be configured for snap-fit engagement between the bone anchor and the prosthesis assembly.

According to a third aspect of the invention, there is provided a prosthesis assembly for orthopaedic implantation, comprising a prosthesis body and an attachment portion coupled to the prosthesis body, wherein the attachment portion comprises an opening having a receiving portion with a first cross-sectional transverse width and a retaining portion having a second cross-sectional transverse width, wherein the second cross-sectional transverse width is less that the first cross-sectional transverse width. Preferably, the prosthesis body is configured for snap-fit engagement with a bone anchor, secured within the bone.

Prosthesis assemblies and systems in accordance with the present invention allow for removal and replacement of an orthopaedic prosthesis without removing or disturbing the bone anchor with which it is affixed to the bone.

Further embodiments are described in the claims as attached.

SHORT DESCRIPTION OF DRAWINGS

The present invention will be discussed in more detail below, with reference to the attached drawings, in which.

FIGS. 5A-E provide plan views of five different openings in accordance with the present invention.

Figure 6:
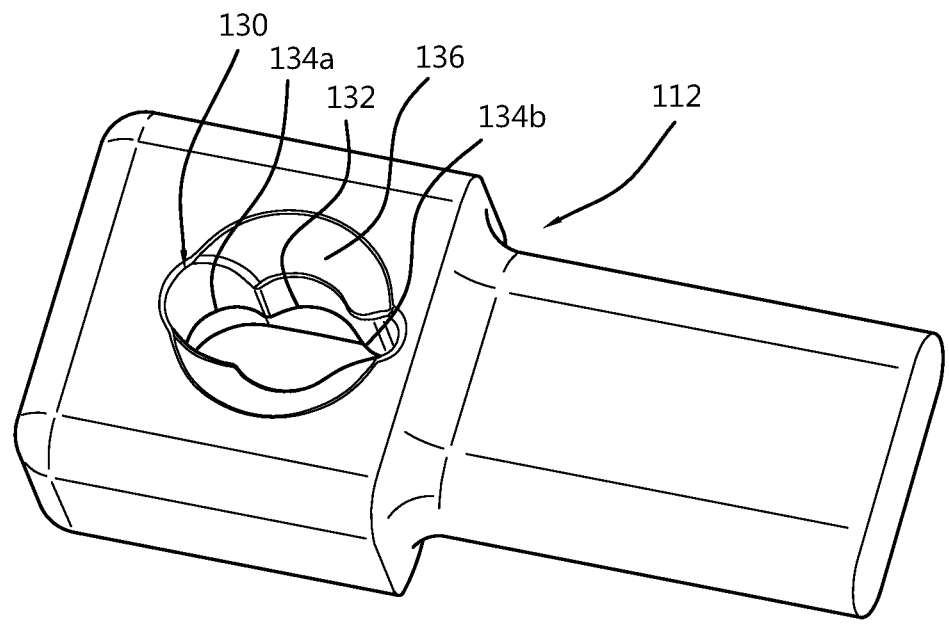

FIG. 6 shows a perspective view of an attachment portion in accordance with an exemplary embodiment of the present invention.

Figure 7A:
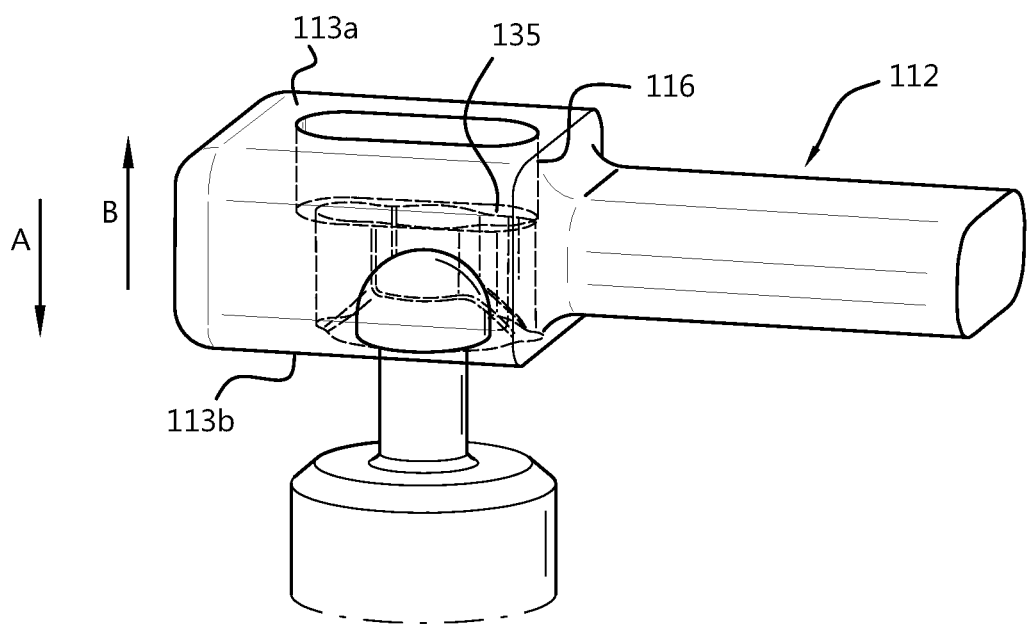
Figure 7B:
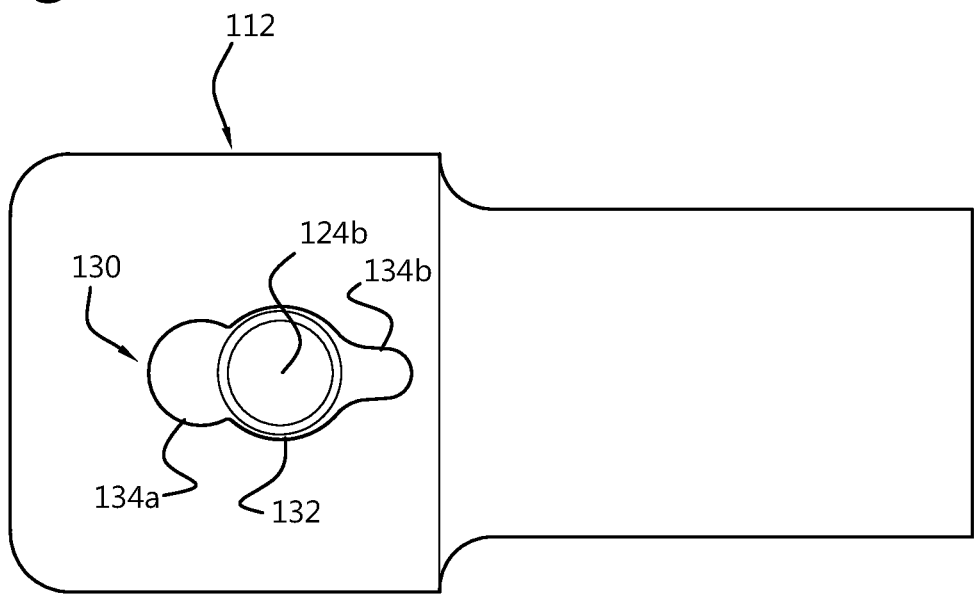
Figure 7C:
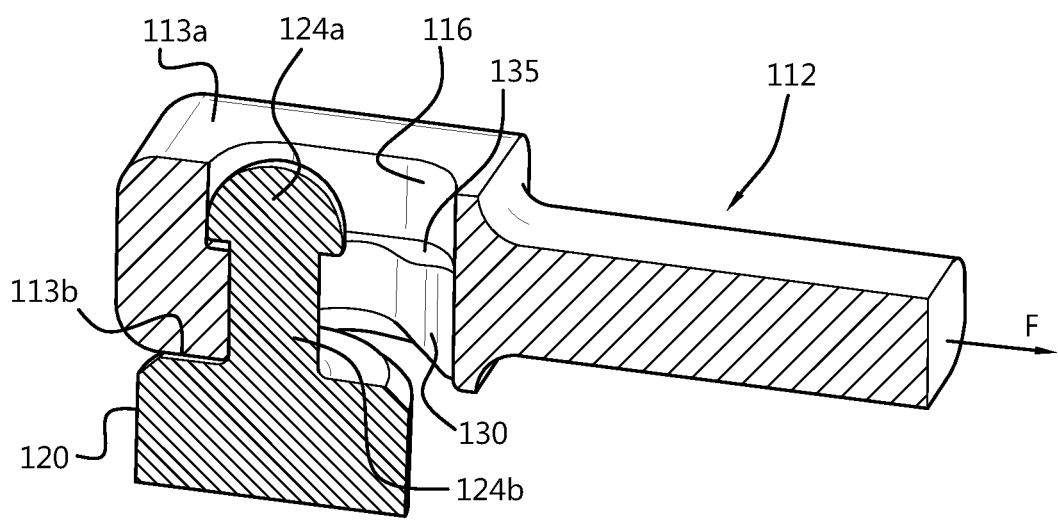

FIGS. 7A-C show the attachment portion of the embodiment shown in FIG. 6, engaged with a fastening member, which provides a snap fit engagement between the prosthesis body and the fastening member.

DESCRIPTION OF EMBODIMENTS

Exemplary embodiments of the present invention will now be described in detail. The skilled person will understand that the devices and methods described herein are non-limiting exemplary embodiments and that the scope of the present invention is defined by the claims. For example, although the present invention will be described in detail in relation to joint prostheses, and particularly meniscus prostheses for the knees, the skilled person will understand that the present invention may be employed in other orthopaedic applications. The features illustrated described in connection with one exemplary embodiment may be combined with features described in other embodiments. Such modifications and variations are included with the scope of the present disclosure.

Figure 1:
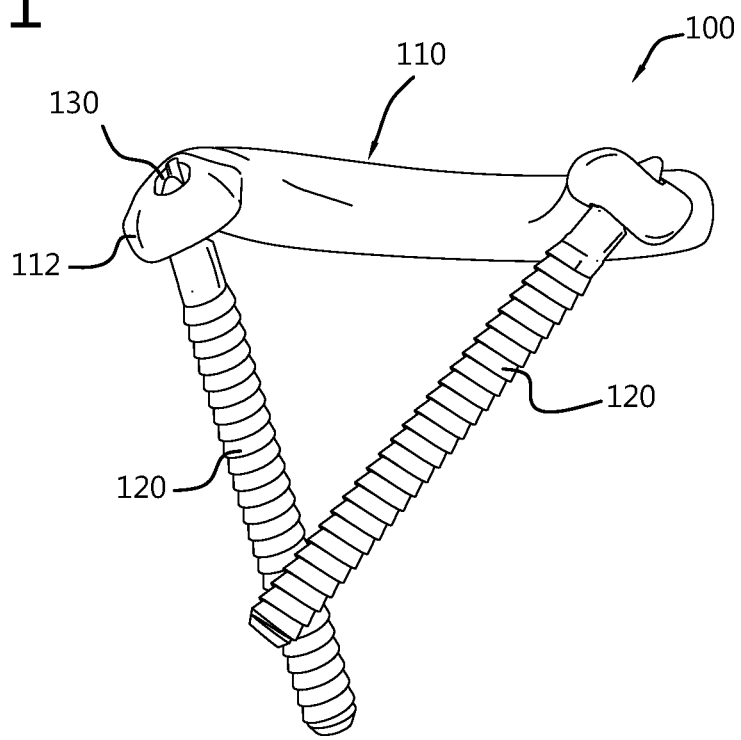
FIG. 1 is a perspective view of a prosthesis system comprising a knee meniscus prosthesis and two bone anchors for securing the prosthesis in place.
Figure 2:
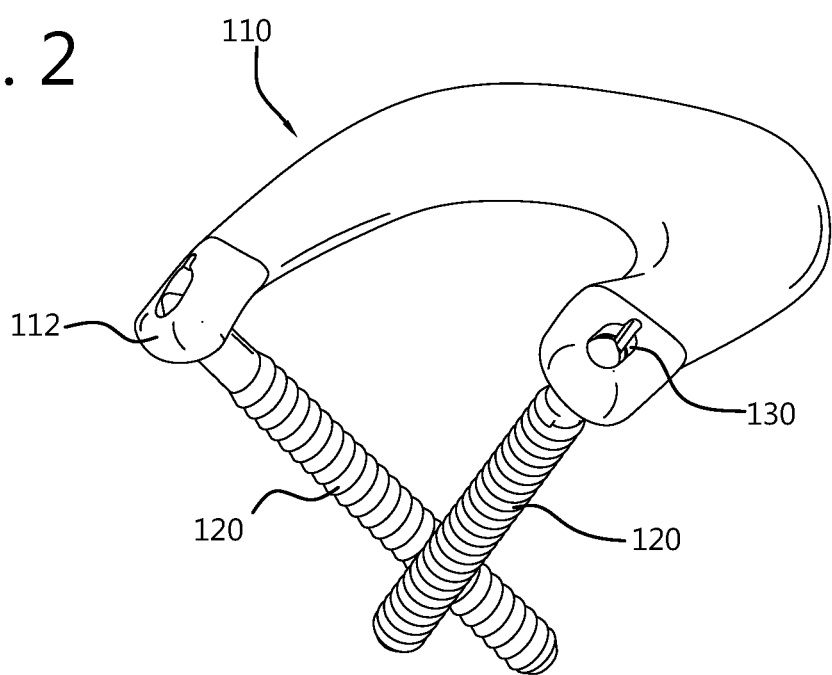
FIG. 2 is a perspective view of the prosthesis system of FIG. 1, showing the apertures in the attachment portions of the meniscus through which the bone anchors extend.

A prosthesis system in accordance with one embodiment of the present invention is shown in FIGS. 1 and 2. The prosthesis system comprising a prosthesis assembly 100 and at least one bone anchor 120. The prosthesis assembly 100 comprises a prosthesis body 110 and an attachment portion 112 coupled to the prosthesis body 110. The attachment portion 112 comprises an opening 130 through which the bone anchor 120 is passed to secure the prosthesis assembly 100 to the bone. The opening 130 has a receiving portion 132 with a first cross-sectional transverse width and a retaining portion 134 extending from the receiving portion 132 (see the description of FIG. 4 below). The retaining portion 134 has a second cross-sectional transverse width, which is less than the first cross-sectional transverse width.

The attachment portion 112 comprises an upper face 113a and a lower face 113b, as explained in more detail below with reference to FIGS. 7A and 7C. The upper face 113a is configured to face away from the bone to which the prosthesis is secured when the prosthesis is in situ. The lower face 113b is configured to face towards the bone to which the prosthesis is secured. The first and second transverse widths above are defined in the plane in which the lower face 113b extends.

In the embodiment shown in FIGS. 1 and 2, the prosthesis body 110 provides an artificial meniscus for a knee joint, or in other words a knee meniscus replacement. The attachment portion 112 comprises a distal end, which is coupled to the prosthesis body 110, and a free proximal end. In the embodiment shown in FIGS. 1 and 2, two attachment portions 112 extend from either end of the prosthesis body 110. However, the skilled person will appreciate that in some applications, one attachment portion will be sufficient, whereas in others, three or more attachment portions may be provided. Each attachment portion 112 comprises an opening 130 in the lower face 113b of the attachment portion 112, which is adapted to be secured to the bone by bone anchor 120.

The bone anchor 120 and the prosthesis body 110 will now be described individually in more detail with respect to FIGS. 3 and 4.

Figure 3:
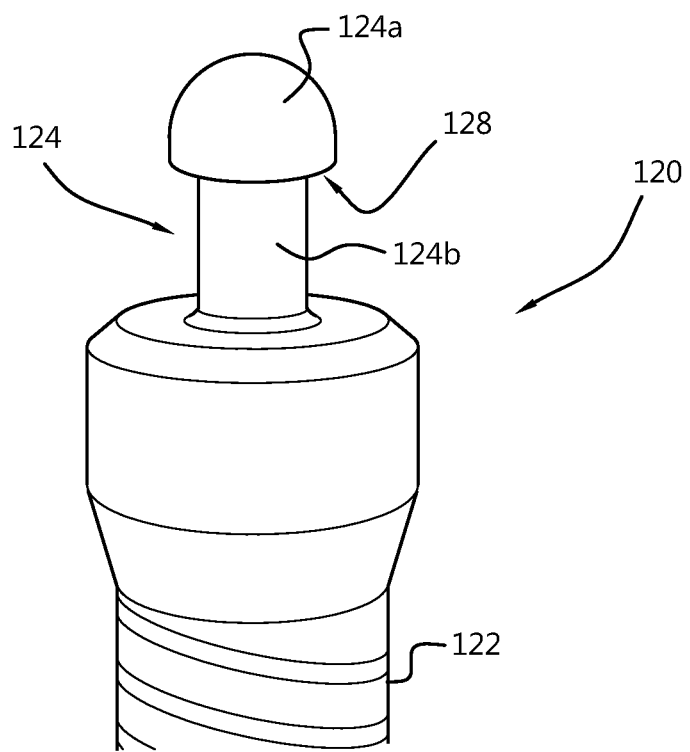
FIG. 3 show a fastening member on a bone anchor in accordance with one embodiment of the present invention.
Figure 4:
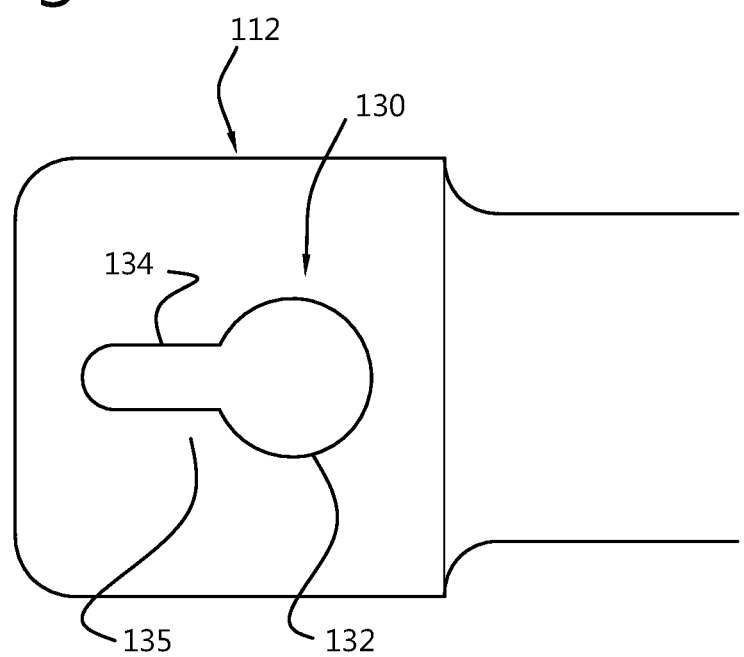
FIG. 4 shows one embodiment of an attachment portion, which comprises an opening for receiving the fastening member of FIG. 3.

FIG. 3 shows an exemplary embodiment of a bone anchor 120 in more detail. The bone anchor 120 comprises a stem 122, which is configured to be secured to a bone or a body structure, and a fastening member 124, which is configured to engage the opening 130 in the prosthesis assembly 100.

The stem 122 of the bone anchor 120 may take many different forms. For example the stem 122 may comprise a rigid body comprising a threaded portion along at least part of its length for securing the bone anchor 120 within a bore provided in the bone. However, the means by which the bone anchor 120 is secured within the bone is not critical to the present invention and other suitable means of securing the bone anchor 120 within the bone will be apparent to the skilled person.

According to embodiments of the present invention, the stem 122 and the fastening member 124 may be formed integrally as a single piece. Alternatively, the stem 122 and the fastening member 124 may be provided as separate components. In such embodiments, the stem 122 may be driven into the bone and secured before the fastening member 124 is coupled thereto. Alternatively, the stem 122 and the fastening member 124 can be fixed to each other before the stem 122 is secured within the bone. The skilled person will understand that the fastening member 124 may be fixed to the stem 122 in different ways. For example, the fastening member 124 may be provided with means for threaded engagement with the stem 122. In general wording, the bone anchor 120 may have multiple parts. The multiple parts can be assembled at various stages of use of the prosthesis system, even when the prosthesis body 110 is already in place. E.g. using a bolt connection between the multiple parts, it is possible to secure the prosthesis body 110 without making use of the flexibility of the attachment portion 112.

The fastening member 124 as shown in FIG. 3 comprises a head 124a and a neck 124b. The neck 124b couples the head 124a to the stem 122 and is relatively narrow compared to the head 124a.

The head 124a may have a rounded profile. For example, the head 124a shown in FIG. 3 has a hemispherical profile. However, the skilled person will appreciate that other shapes provide a suitable engagement feature for holding the prosthesis assembly 100 in place. For example, a substantially conical (or even cuboidal) head may be provided. Shapes that taper from a relatively wide base to a relatively narrow tip are advantageous because they facilitate proper alignment with the opening 130.

In exemplary embodiments, the head 124a of fastening member 124 meets the neck 124b to form a substantial planar engagement surface 128 for abutment with a corresponding surface on the attachment portion 112 of the prosthesis assembly 100. In other words, the stepped profile of the fastening member 124 forms an engagement surface 128. The abutment of the engagement surface 128 with an abutment surface 135 formed by the rim of the opening 130 provides a latching engagement that prevents removal of the fastening member 124 from the opening 130. The skilled person will appreciate that the same effect can also be achieved with other geometries. For example, the engagement surface 128 may be inclined toward the neck 124b. The rim of the opening 130 may or may not be formed with a complementary inclined surface.

The bone anchor 120 can be formed of any suitable biocompatible material, e.g. stainless steel, titanium or a polymer material. The choice of material allows to further select the proper material properties needed for the bone anchor 120, such as high yield strength, high wear resistance, high fatigue limit and biocompatibility.

The opening 130 provided in the attachment portion 112 for receiving the fastening member 124 will now be described in more detail with reference to FIG. 4. As shown in FIG. 4, the opening 130 formed in the lower face 113b of the attachment portion 112 comprises a continuous opening having a receiving portion 132 and a retaining portion 134. The retaining portion 134 is relatively narrow compared to the receiving portion 132. The retaining portion 134 is surrounded by an abutment surface 135. In the system described above with reference to FIGS. 1 and 2, the receiving portion 132 is dimensioned to allow the head 124a of the fastening member 124 to pass through the opening 130. However, whilst the relatively narrow retaining portion 134 is dimensioned to accommodate the neck 124b of the fastening member 124, the relatively narrow opening of the retaining portion 134 prevents the head 124a of the fastening member 124 passing through the opening 130 because the engagement surface 128 of the head 124a abuts the abutment surface 135 surrounding the retaining portion 134. Thus the attachment portion 112 is confined between the head 124a and the bone into which the stem 122 is driven. In the exemplary embodiment of the present invention shown in FIGS. 1 and 2, the prosthesis body 110 has a wedge shaped cross-section, which mimics the cross section of knee meniscus. The wedge shaped form of the prosthesis body 110 means that as a load is applied to the joint, the prosthesis body 110 is extruded from the joint. This applies tension to the attachment portion 112, moving the attachment portion 112 relative to the bone anchor 120 such that the neck 124b slides along the opening from the receiving portion 132 to the retaining portion 134 of the opening 130. Thus, when in situ the fastening member 124 engages the retaining portion 134 of the opening 130, which has a smaller diameter than the receiving portion 132. Since the head 124a has a greater diameter than the width of the opening 130 in the retaining portion 132, the attachment portion 112 is secured between the head 124a and the bone.

The retaining portion 134 is at least partially surrounded by an abutment surface 135 for abutting the corresponding engagement surface 128 on the fastening member 124, thereby preventing the head 124a from passing through the opening 130. The abutment surface 135 may be parallel to the plane defined by the lower face 113b of the attachment portion 112 in which the opening 130 is formed.

As illustrated in FIGS. 5A-E, the opening 130 can take many forms. For example, the opening 130 may resemble a conventional keyhole, with a substantially circular receiving portion 132 and a straight narrow slot extending therefrom, which provides the retaining portion 134 (see FIG. 5A). In general, the retaining portion 134 is straight or curved, or the receiving portion 132 tapers continuously into the retaining portion 134.

Figure 5A:
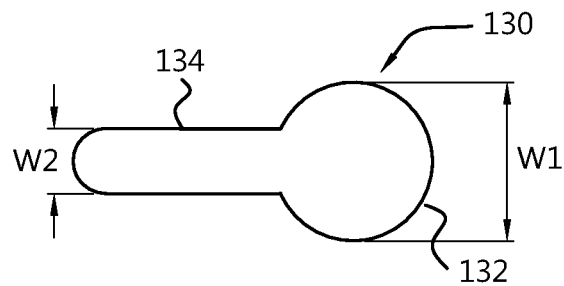
Figure 5B:
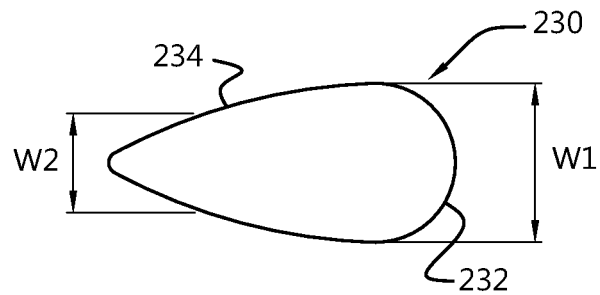

In another embodiment, the opening may comprise an opening 230 that tapers continuously from a relatively wide receiving portion 232 at one end to a relative narrow retaining region at the other 234 (see FIG. 5B). Although the fastening member 124 can pass through the widest part of the aperture 230, the narrowest part of the opening 230 will not allow the head 124a of the fastening member 124 to pass there through.

Figure 5C:
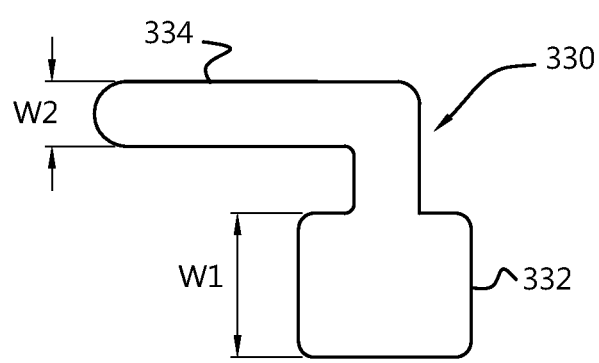

In yet another embodiment, the opening 330 can comprise an L-shaped retaining portion 334 (see FIG. 5C). In this embodiment, the fastening member 124 must be slid about a 90 degree bend to reach the retaining portion 334. This arrangement may be used in applications in which tension within the joint cannot be relied upon to secure the fastening member 124 in the retaining portion 334. The skilled person will understand that the 90 degree bend shown in FIG. 5C is on exemplary embodiment, and that the retaining portion 334 can follow other paths.

Figure 5D:
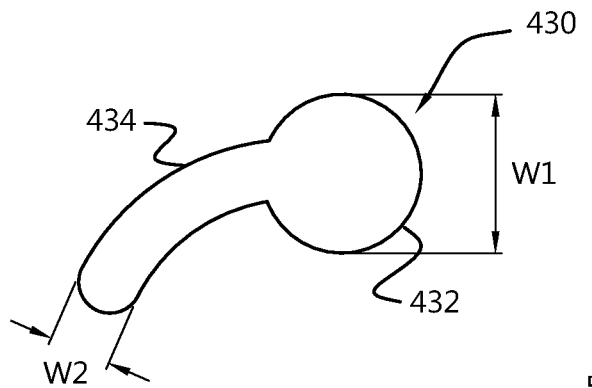

In yet another embodiment, an opening 430 can comprise a retaining portion 434 that is curved (see FIG. 5D). These embodiments may be suitable for applications in which the opening 430 must follow a curved trajectory of an attachment portion on a prosthesis.

In some embodiments, the opening 530 can comprise more than one retaining portion e.g. the opening 530 may comprise first and second retaining portions 534a and 534b. In such exemplary embodiments, the opening 530 may comprise a central receiving portion 532 and two opposing retaining portions 534a, 534b extending from either side of the receiving portion 532. One advantage of diametrically opposed retaining portions is that the prosthesis is securely fastened when tension is applied in one of two opposite directions. Moreover, multiple retaining portions 534a, 534b (and e.g. 134a, 134b in the embodiments shown in FIGS. 6 and 7B) extending from a single receiving portion may allow the opening 530 to flex to provide a snap fit engagement with a fastening member 124. However, this is not essential to achieve snap fit engagement between the fastening member 124 and the prosthesis assembly 100. Snap fit engagements of the fastening member 124 within the opening 530 will be discussed in more detail in the following paragraphs, with particular reference to FIGS. 6 and 7A-C.

In any of the above embodiments described with reference to FIGS. 5A to 5E, it can be advantageous to provide an opening 130 in which the proximal end of the retaining portion 134 is rounded. This can ensure smooth rotation of the prosthesis assembly 100 about the neck 124b of fastening member 124 and improve the longevity of the implant.

Figure 5E:
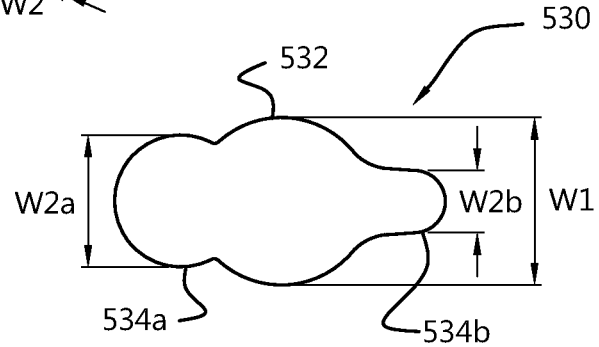

In embodiments with two relatively narrow retaining portions 534a, 534b extending either side of the receiving portion, it will be appreciated that the retaining portions need not be arranged symmetrically. For example, the retaining portions may differ from each other in terms of width, length and shape. As shown in FIG. 5E, the opening 530 may comprise a first generally circular receiving portion 532, a first retaining portion 534a having a generally circular shape, with a smaller diameter than the receiving portion 532, and a second retaining portion 534b having generally straight profile.

In all of the above described embodiments, the opening 130 comprises a relatively wide receiving portion 132 through which the head 124a of the fastening member 124 can pass, and a relatively narrow retaining portion 134 through which the head 124a of the cannot pass. This ensures that the fastening member 124 can only be removed from the opening 130 when it is aligned with the receiving portion 132. Put another way, the receiving portion 132 has a first transverse cross-sectional width W1 and the retaining portion 134 has a second transverse cross-sectional width W2 which is less than the first cross-sectional width W1. It is noted that in the exemplary embodiments of FIGS. 5E, 6 and 7B, the retaining portion 134 has multiple retaining portions, which each may have a different width W2a, W2b. The skilled person will understand that the transverse cross-section is then defined by the lower face 113b of the attachment portion 112 in which the opening 130 is formed. The widths W1 and W2 are defined perpendicular to the path defined by the opening 130 along which the fastening member 124 can travel. The asymmetric profile of the fastening member 124 prevents the head 124a from being easily removed from the opening 130. This is due to the abutment of the engagement surface 128 on the fastening member 124 and the abutment surface 135 surrounding the opening 130.

The skilled person will recognise that the particular shape of the retaining portion 134, the location of the attachment portion 112 and the orientation of the opening 130 with respect to the prosthesis body 110 can be optimised based on the intended use of the implant.

For example, in situ the wedge shaped cross-section of a healthy knee meniscus redistributes compressive loads within the knee joint into tensile forces around its circumference, reducing contact stresses in the joint and preserving the articulation surface of the knee. A prosthetic knee meniscus according to the present invention can utilise the tension experienced during loading to securely hold the prosthesis in place. By proving an opening 130 towards the free ends of horns of a prosthesis meniscus (i.e. in the attachment portions 112 of the prosthesis body 110 as described with reference to the exemplary embodiments above), the tension naturally present during loading can be employed to slide the fastening member 124 towards the retaining portion 134 of the opening 130. To facilitate this sliding motion, the opening 130 can be oriented with its longitudinal axis along the longitudinal axis of the horn. As shown in FIG. 4, the receiving portion 132 is positioned distal to the retaining portion 134. In other words, the retaining portion 134 is oriented toward the free end of the horn. Once apprised of the present invention, the skilled person will be able to determine the optimal shape/location/orientation of the opening 130 for a variety of orthopaedic procedures. In a further advantageous embodiment, the prosthesis body 110 has a wedge-like shape, such that during use, the wedge shape of the prosthesis body 110 forces the meniscus prosthesis assembly 100 towards the outside of the knee joint. This will force the attachment portion 112 more medially, driving the neck 124b of fastening member 124 towards the retaining portion 134.

In all of the exemplary embodiments of the invention described above, the opening 130 in the prosthesis assembly 100 may be configured with a receiving portion 132 dimensioned to allow passage of a fastening member 124 there through without deformation of the opening 130.

Alternatively, the opening 130 can be configured to provide a snap fit engagement of the prosthesis assembly 100 with the fastening member 124. In these exemplary embodiments, the inner dimensions of the receiving portion 132 are slightly smaller than the outer dimensions of the fastening member 124. However, the material in which the opening 130 is formed is sufficiently flexible to allow the opening 130 to flex to accommodate the head 124*a*, before returning to its original shape. This flexibility allows the opening 130 to deform to provide a snap fit engagement with the fastening member 124. In such embodiments, the engagement surface 128 of the head 124*a* engages the abutment surface 135 surrounding the opening 130 when it is aligned with the retaining portion 134 and when it is aligned with the receiving portion 132. This means that the head 124*a* cannot pass through the receiving portion 132 of the opening 130 unless sufficient force is applied to flex the opening 130. Due to the asymmetric shape of the head 124*a*, the force required to remove the head 124*a* from the opening 130 is greater than the force required to engage the head 124*a* with the opening 130. The hemispherical or conical head 124*a* described with reference to FIG. 3 aids the snap fit engagement of the fastening member 124 within the opening 130 because the tapered head 124*a* allows relatively easy insertion of the head 124*a* into the opening 130. However, once the head 124*a* has passed through the opening 130, the engagement surface 128 provides a latching engagement with the abutment surface 135 formed by the rim of the opening 130 and prevents removal of the head 124*a* from the opening 130. As tension is applied to the prosthesis in situ when the knee is loaded during walking or weight bearing, the fastening member 124 slides along the opening 130 towards the narrower retaining portion(s) and becomes even more securely locked in the narrower retaining portion 134 of the opening 130. Moreover, since the surface of the head 124*a*, which is partially in contact with the abutment surface 135 surrounding the opening 130 has a large surface area compared to the neck 124*b*, the contact pressure in between head 124*a* and the attachment portion 112 is significantly reduced, therefore increasing the wear performance and life span of the implant.

The skilled person will appreciate that the snap fit embodiment described above may also allow for snap removal of prosthesis assembly 100, should the prosthesis require replacement. It will be understood that to maximise the durability of the present invention, prosthesis assembly 100 can be advantageously configured such that the magnitude and/or direction of the force required to remove the head 124*a* from the receiving portion 132 differs from the loads likely to be experienced by the prosthesis in situ. For example, the force required to remove the head 124*a* from the receiving portion 132 of the opening 130 should exceed the forces likely to be applied to the implant during normal use. Additionally or alternatively, the force that must be applied to remove the head 124*a* from the receiving portion 132 may have a different directional component (e.g. be in an opposite direction to the forces experienced by the implant during normal loading within a joint. Once apprised of the present disclosure, the skilled person will be able to adapt the opening 130 to depending on the desired application. For example, the skilled person can choose the precise dimensions of the opening, the modulus of the materials and the relative orientation of the retaining portion and the receiving portion to meet the mechanical requirements of the anatomical application.

One possible exemplary embodiment will now be described with reference to FIG. 6. As shown in FIG. 6, the attachment portion 112 comprises an opening 130 having the profile shown in FIG. 5E. The opening 130 comprises a central receiving portion 132, with first and second retaining portions 134*a* and 134*b* extending from opposing sides thereof, similar to the embodiment shown and described with reference to FIG. 5E. The attachment portion 112 comprises a polycarbonate urethane, which provides the required flexibility to allow snap fit engagement with a rigid fastening member 124. The attachment portion 112 is configured for use with the fastening member 124 shown in FIG. 3. The receiving portion 132 has a diameter that is approximately 10% smaller than the diameter of the head 124*a* of the fastening member 124 at its widest part. The retaining portions 134*a* and 134*b* extend from either side of the receiving portion 132 to provide the opening 130 with a total length L of approximately twice the diameter of the head 124*a*. The force required to push the head 124*a* through the receiving portion 132 of the opening is in the region of 50N, preferably between 10N and 100N, more preferably between 20N and 80N, more preferably between 40N and 60N, and most preferably approximately 50N.

As shown in FIG. 6, the opening 130 can be further adapted to facilitate correct placement and engagement of the head 124*a* with the attachment portion 112. For example, the opening 130 may comprise a tapered or flared opening 136. This shape can help to guide the fastening member 124 towards the receiving portion 132 of the opening. Since the fastening member 124 of the bone anchor 120 is on the lower face 113*b* of the attachment portion 112 (i.e. behind the prosthesis during placement), the head 124*a* must often be aligned with the receiving portion 132 in a position that cannot readily be seen by the surgeon (unlike conventional fixation means in which the bone anchor 120 is driven through the prosthesis from the front). This feature can therefore provide much needed help in correctly positioning the attachment portion 112 for coupling to the fastening member 124.

Referring now to FIGS. 7A and 7B, the attachment portion 112 may also comprise a recess 116 that accommodates the head 124*a* of the fastening member 124 so that it does not protrude from the upper face 113*a* of the attachment portion 112 or protrudes to a lesser extent. The recess 116 is provided by a stepped bore that extends through the attachment portion 112. In such embodiments, the abutment surface 135 is provided by the step within the bore. The bore towards the upper face 113*a* of the attachment portion 112 comprises a channel that can accommodate the head 124*a* of the fastening member 124 along its length, whereas the bore at the lower face 113*b* of the attachment portion 112 comprises the relatively wide receiving portion 132 and a relatively narrow retaining portion 134, as described above. Providing a recess 116 to accommodate the head 124*a* of the fastening member 124 can be advantageous because it reduces the overall size of the prosthesis, which is valuable in joint prosthesis applications. It may also reduce the likelihood of the head 124*a* becoming damaged or causing damage within the joint. Although embodiments comprising a recess 116 for accommodating the head 124*a* of the fastening member 124 have associated advantages, the skilled person will appreciate that an opening 130 having a straight sided bore (without recess 116) can be used. In such embodiments, the engagement surface 128 of the head 124*a* simply abuts the upper face 113*a* of the attachment portion 112.

In the exemplary embodiments shown in FIGS. 1 to 4, 6 and 7, the opening 130 is formed as a through bore. However, the skilled person will appreciate that opening 130 may be formed as a blind bore. In such embodiments, the attachment portion 112 is formed with a stepped bore, as described above with reference to FIGS. 7A and 7B. However, in a blind bore embodiment, the upper surface 113a of the attachment portion 112 is closed such that channel for accommodating the head 124a of the fastening member 124 is enclosed. In embodiments comprising a blind bore, a flared opening 136 may also be provided to facilitate correct placement of the opening 130 with respect to the fastening member 124. In blind bore embodiments, the head 124a is completely hidden within the attachment portion 112 when the prosthesis is in place.

In even further embodiments, the attachment portion 112 has multiple parts. The multiple parts may be arranged to make a snap fit connection by different means than flexibility of the material of the attachment portion 112 itself, e.g. using an additional (flexible) insert clamped into the opening 130.

Placement and replacement of a prosthesis according to one exemplary embodiment of the present invention will now be described with reference to FIGS. 7A-C.

The surgical procedure for using a joint prosthesis assembly according to one exemplary embodiment of the present invention is as follows. A knee meniscus prosthesis assembly according to the present invention is provided. Under guidance of arthroscopic view the exact anatomic position of the anterior and posterior attachment of the meniscus are determined. With an aiming device a hole is drilled towards or from the point of the anatomic meniscus horn attachments in the joint. A bone anchor 120 is secured within the drilled hole. The bone anchor 120 may be integrally formed with a fastening member 124 at its distal end or it may comprise attachment means for securing a fastening member 124 thereto. Once the bone anchor 120 and the fastening member 124 are secured in place, the knee meniscus prosthesis assembly 100 can be attached. The meniscus prosthesis assembly 100 is placed in the joint with the recess 116 placed on the head 124a of the fastening member 124 and with a tool (e.g. a (trip) lever) the polymer prosthesis assembly 100 is pushed on the bone anchor 120.

As shown in FIG. 7A, the meniscus prosthesis assembly 100 is oriented in the joint such that an opening 130 on one attachment portion 112 is aligned with the head 124a of the fastening member 124. The flared opening 136 guides the fastening member 124 to the correct position relative to the opening 130, i.e. towards the receiving portion 132 of the opening 130. The attachment portion 112 is formed of a flexible material, e.g. a flexible, biocompatible, non-resorbable polymer. Once the fastening member 124 is aligned with the receiving portion 132 of the opening 130, force is applied to the attachment portion 112 in the direction of arrow A. Under force in the direction of arrow A, the curved surface of the head 124a engages the flared opening 136 until the flexible material of the attachment portion 112 flexes, without being deformed permanently, to allow the head 124a to pass through the receiving portion 132 of the opening 130. As shown more clearly in FIG. 7B, the retaining portion 134 may be provided on two sides of the opening 130, which allow a more easy flexing of the part of the attachment portion 112 surrounding the opening 130. The left side of retaining portion 134 has a width allowing accommodation of the neck 124b of the fastening member 124, while the right side 134b is smaller, and only serves to allow flexing of the opening 130.

As shown in FIG. 7B, once the head 124a of the fastening member 124 has passed through the receiving portion 132, the flexible material in which the opening 130 is formed returns to its original configuration such that the abutment surface 135 surrounding the opening 130 engages the engagement surface 128 of the head 124a, thereby providing snap fit engagement of the fastening member 124 and the opening 130. Once seated in the position shown in FIG. 7B, the fastening member 124 cannot easily be removed from the receiving portion 132 of the opening 130 due to the latching engagement between the engagement surface 128 of the fastening member 124 and abutment surface 135 provided by the rim of the opening 130.

The prosthesis assembly comprises a biocompatible, non-resorbable material. It may comprise one or more of polycarbonate urethane(s), polyethylene(s), cross-linked polyethylene(s), polyethylene terephthalate (s), polyether ether ketone(s). Preferably, at least the attachment portion comprises a material having a tensile modulus of more than 100 MPa, as determined by ISO 527-1. The material that forms the attachment portions may extend all the way through the prosthesis body to provide a reinforcement part. The reinforcement part and the attachment portions can be formed as a single part, and the prosthesis can further comprise a softer material covering the material that forms the attachment portions and the reinforcing part. The softer material can have a tensile modulus of at most 100 MPa, as determined by ISO 527-1.

European Patent Application No. EP15708537.4 provides a detailed description of a prosthesis assembly in which the present invention may be implemented to provide particularly advantageous assembly. The entirety of this document is incorporated by reference and the skilled person will appreciate that embodiments of the present invention include a prosthesis assembly as described in EP15708537.4, comprising attachment portions having openings as described above.

Referring now to FIG. 7C, as tension is applied to the knee meniscus in the direction of arrow F (either by the surgeon or by natural loading across the joint due to the wedge shape of the prosthesis), the attachment portion 112 slides horizontally along the fastening member 124 such that the fastening member 124 moves along the opening 130 towards retaining portion 134. Since the retaining portion 134 of the opening 130 will not allow the head 124a to pass there through (even accounting for the flexibility of the material of attachment) tension applied to the attachment portion 112 securely locks the prosthesis in place. The above steps can be repeated for the attachment portion 112 at the other end of the meniscus prosthesis assembly 100.

Should the meniscus prosthesis assembly 100 become damaged and require replacement, the present invention allows removal and replacement of a knee prosthesis assembly 100 without disturbing the bone anchor 120 or the fastening member 124 that holds the prosthesis in place. Instead, the surgeon can apply tension to the free end of the attachment portion 112 to align the head 124a with the receiving portion 132 of the opening 130 as shown in FIG. 7B. Once aligned with the relatively wide receiving portion 132 of the opening 130, force applied to the attachment portion 112 in a direction B (illustrated in FIG. 7A) allows the opening 130 to flex, and release the fastening member 124 from the confines of the opening 130. A new prosthesis assembly 100 can then be easily snapped into place as described above.

The present invention has been described above with reference to a number of exemplary embodiments as shown in the drawings. Modifications and alternative implementations of some parts or elements are possible, and are included in the scope of protection as defined in the appended claims.

The invention claimed is:

1. A prosthesis assembly for orthopaedic implantation comprising:
   a prosthesis body having a wedge-like shape comprising an anterior-facing end and a posterior-facing end,
   at least one attachment portion coupled to the prosthesis body, wherein the at least one attachment portion comprises an opening having a receiving portion with a first cross-sectional transverse width and a retaining portion extending from the receiving portion in a direction parallel to a plane defined by a bone-engaging lower face of the at least one attachment portion in which the opening is formed, the retaining portion having a second cross-sectional transverse width, which is less than the first cross-sectional transverse width,
   wherein the at least one attachment portion has a distal end coupled to one end of the prosthesis body and a free proximal end,
   wherein the opening is oriented such that the receiving portion is positioned distal to the retaining portion,
   wherein the at least one attachment portion is configured for engagement with a fastening member of a bone anchor, through the opening,
   wherein the prosthesis body is a knee meniscus replacement.

2. The prosthesis assembly according to claim 1, wherein the opening comprises a further retaining portion extending from the receiving portion.

3. The prosthesis assembly according to claim 1, wherein the opening is formed as a through bore or a blind bore.

4. The prosthesis assembly according to claim 1, wherein the at least one attachment portion is configured for snap-fit engagement with the fastening member of the bone anchor, through the opening.

5. The prosthesis assembly according to claim 1, wherein the at least one attachment portion provides an abutment surface at least partially surrounding the opening that provides for abutting a corresponding engagement surface on the fastening member and wherein the abutment surface is parallel to the plane defined by the bone-engaging lower face of the at least one attachment portion in which the opening is formed.

6. The prosthesis assembly according to claim 1, wherein the receiving portion comprises a tapered or flared opening.

7. The prosthesis assembly according to claim 1, wherein a proximal end of the retaining portion is rounded.

8. The prosthesis assembly according to claim 1, wherein the retaining portion is straight or curved or wherein the receiving portion tapers continuously into the retaining portion.

9. The prosthesis assembly according to claim 1, wherein the at least one attachment portion is flexible.

10. The prosthesis assembly according to claim 1, wherein the at least one attachment portion has multiple parts.

11. A prosthesis system comprising:
    the prosthesis assembly according to claim 1, and
    a bone anchor, wherein the bone anchor comprises a fastening member configured to engage the opening in the at least one attachment portion of the prosthesis assembly and a stem configured to be secured to a bone of the knee joint.

12. The prosthesis system according to claim 11, wherein the fastening member of the bone anchor comprises a rounded profile.

13. The prosthesis system according to claim 12, wherein the fastening member of the bone anchor comprises a hemispherical profile.

14. The prosthesis system according to claim 11, wherein the bone anchor has multiple parts.

* * * * *